US011250936B1

(12) United States Patent
Keen et al.

(10) Patent No.: US 11,250,936 B1
(45) Date of Patent: *Feb. 15, 2022

(54) UNIVERSAL APPLICATION INTEGRATOR

(71) Applicant: ALLSCRIPTS SOFTWARE, LLC, Chicago, IL (US)

(72) Inventors: Ronald Keen, Shelburne, VT (US); Thomas K. Bissonette, South Burlington, VT (US); Stanley Crane, Chicago, IL (US)

(73) Assignee: ALLSCRIPTS SOFTWARE, LLC, Chicago, IL (US)

( * ) Notice: Subject to any disclaimer, the term of this patent is extended or adjusted under 35 U.S.C. 154(b) by 164 days.

This patent is subject to a terminal disclaimer.

(21) Appl. No.: 16/450,874

(22) Filed: Jun. 24, 2019

Related U.S. Application Data

(63) Continuation of application No. 12/014,758, filed on Jan. 15, 2008, now Pat. No. 10,332,620.

(60) Provisional application No. 60/884,998, filed on Jan. 15, 2007.

(51) Int. Cl.
*G16H 10/60* (2018.01)

(52) U.S. Cl.
CPC .................... *G16H 10/60* (2018.01)

(58) Field of Classification Search
CPC ........ G16H 10/60; G16H 20/40; G16H 40/20; G16H 70/20
USPC ............................................................ 705/3
See application file for complete search history.

(56) References Cited

U.S. PATENT DOCUMENTS

| 6,523,009 | B1 | 2/2003 | Wilkins |
| 7,349,858 | B1 | 3/2008 | Mcgrady et al. |
| 7,949,545 | B1 | 5/2011 | Madras |
| 2001/0051879 | A1 | 12/2001 | Johnson et al. |
| 2002/0116222 | A1 | 8/2002 | Wurster |
| 2003/0105389 | A1 | 6/2003 | Noonan et al. |
| 2003/0163351 | A1 | 8/2003 | Brown et al. |
| 2004/0122709 | A1 | 6/2004 | Avinash et al. |
| 2004/0199404 | A1 | 10/2004 | Ripperger et al. |

(Continued)

FOREIGN PATENT DOCUMENTS

WO    WO-2009008968 A1 * 1/2009 ............. G16H 70/20

OTHER PUBLICATIONS

Yun Sik Kwak, "International standards for building Electronic Health Record (EHR)," Proceedings of 7th International Workshop on Enterprise networking and Computing in Healthcare Industry, 2005. Healthcom 2005., 2005, pp. 18-23, doi: 10.1109/HEALTH.2005.1500373 (Year: 2005).*

(Continued)

*Primary Examiner* — Hiep V Nguyen
(74) *Attorney, Agent, or Firm* — Loza & Loza, LLP; Peter Zura

(57) ABSTRACT

A universal application integrator system enables the automated integration of data from patient care devices into electronic health records (EHRs). In addition, the system acts as a context manager between these patient care devices, EHR applications, and ancillary specific patient care applications. The system is the central controller for direct integration with patient care devices. This allows for click-once implementation and automated driver uploads for patient care devices. Third party application integration allows for device and patient context information to be shared among applications in a standardized patient care fashion.

21 Claims, 3 Drawing Sheets

(56) References Cited

U.S. PATENT DOCUMENTS

| | | |
|---|---|---|
| 2004/0254816 A1 | 12/2004 | Myers |
| 2005/0021512 A1 | 1/2005 | Koenig |
| 2005/0065816 A1* | 3/2005 | Limberg ............... G06Q 30/04 705/2 |
| 2005/0071194 A1 | 3/2005 | Bormann et al. |
| 2005/0075544 A1 | 4/2005 | Shapiro et al. |
| 2006/0122864 A1 | 6/2006 | Gottesman et al. |
| 2006/0212317 A1 | 9/2006 | Hahn et al. |
| 2006/0229909 A1 | 10/2006 | Kaila et al. |
| 2006/0235280 A1 | 10/2006 | Vonk et al. |
| 2006/0277070 A1 | 12/2006 | Hungerford et al. |
| 2007/0043596 A1 | 2/2007 | Donaldson et al. |
| 2007/0136218 A1* | 6/2007 | Bauer .................... G16H 40/67 706/12 |
| 2007/0162310 A1 | 7/2007 | Schmidt |
| 2007/0175980 A1 | 8/2007 | Alsafadi |
| 2007/0185738 A1 | 8/2007 | Anuszewski et al. |
| 2008/0077433 A1 | 3/2008 | Kasprisin et al. |
| 2008/0103833 A1 | 5/2008 | Miglietta et al. |

OTHER PUBLICATIONS

PCT/US2008/05110. International Search Report & Written Opinion (dated May 16, 2008).

* cited by examiner

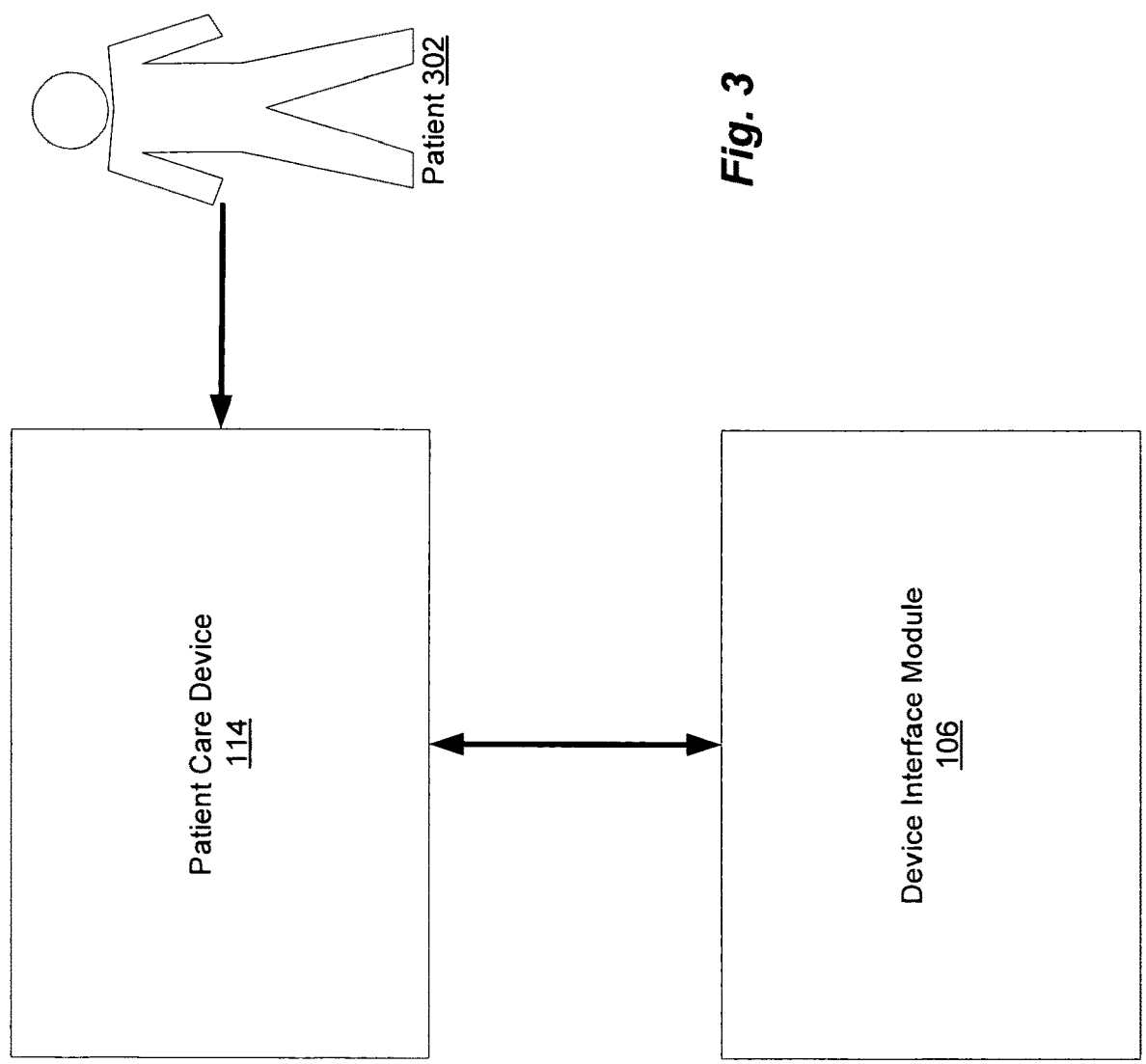

UNIVERSAL APPLICATION INTEGRATOR

CROSS-REFERENCE TO RELATED APPLICATIONS

This application claims the benefit of U.S. Non-Provisional patent application Ser. No. 12/014,758, filed on Jan. 15, 2007, which claims priority to U.S. Provisional Application No. 60/884,998, filed on Jan. 15, 2007, and which are incorporated by reference herein in their entirety.

BACKGROUND OF THE INVENTION

Field of the Invention

The present invention relates generally to the field of electronic health records. In particular, the present invention is directed to a universal application integrator for automatically populating an electronic health record, and driving workflow automation to and from multiple clinical applications and devices that interface with the patient.

Description of the Related Art

Health care providers throughout the country are moving toward maintaining patient records electronically. These electronic health records (EHR) provide several advantages over paper-based records. For example, they can be accessed more rapidly by a health care provider; records do not need to be shipped from department to department to follow a patient throughout a facility; patients can be granted online access to their records, etc.

In order to populate an EHR, patient information must be entered into the record at some point during or following a visit. Patient information that is used to populate an EHR includes patient bibliographic information, narrative data, and vital statistics data. Bibliographic information includes information such as a patient's name, date of birth, address, and the like. Narrative data includes notes dictated or directly entered by a healthcare professional about the patient's condition. Vital statistics include data measured and recorded about a patient's condition—for example, the patient's heart rate, blood pressure, and temperature. Measured vital data can also include the results of an ECG, ultrasound or other test that provides data. Typically, vital statistics data (also referred to as "vitals") are recorded and then manually entered into the patient's EHR.

According to the American College of Clinical Engineering (ACCE) and IHE, there are 1500 patient care device manufacturers with over 3500 different products. Each of these clinical devices captures information from patients that needs to be disseminated to the caregiver; currently, much of that information is delivered in a non-standardized fashion.

Further, patient care workflow can involve many different healthcare professionals such as nurses, doctors, lab technicians and technologists all capturing data on patient care devices and from different applications detached from the providers who determine care. Since this data is currently not captured in real time and disseminated to the clinical decision makers in real-time, patient safety can suffer.

Many patient care devices such as vitals monitors include USB or serial communication ports in order to allow the device to be connected to a computer for printing the stored vitals. However, since these devices typically have no notion of which patient is attached to the device, the readouts and paper that are currently manually captured can be mixed up between patients. Even for those devices that do allow some integration, there is currently no provision to automatically link the data to a current patient encounter.

SUMMARY

The present invention provides a universal application integrator system that enables the automated integration of data from patient care devices into electronic health records (EHRs). In addition, the system acts as a context manager between these patient care devices, EHR applications, and ancillary specific patient care applications. The system is the central controller for direct integration with patient care devices. This allows for click-once implementation and automated driver uploads for patient care devices. Third party application integration allows for device and patient context information to be shared among applications in a standardized patient care fashion.

BRIEF DESCRIPTION OF THE DRAWINGS

FIG. 3 illustrates acquisition of patient diagnostic data from a patient care device in accordance with an embodiment of the present invention.

The figures depict preferred embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF THE PREFERRED EMBODIMENTS

The present invention provides a universal application integrator (UAI) that enables the automated integration of data from patient care devices into electronic health records (EHRs). In addition, the UAI also acts as a context manager between these patient care devices, EHR applications, and ancillary specific patient care applications.

Figure 1:
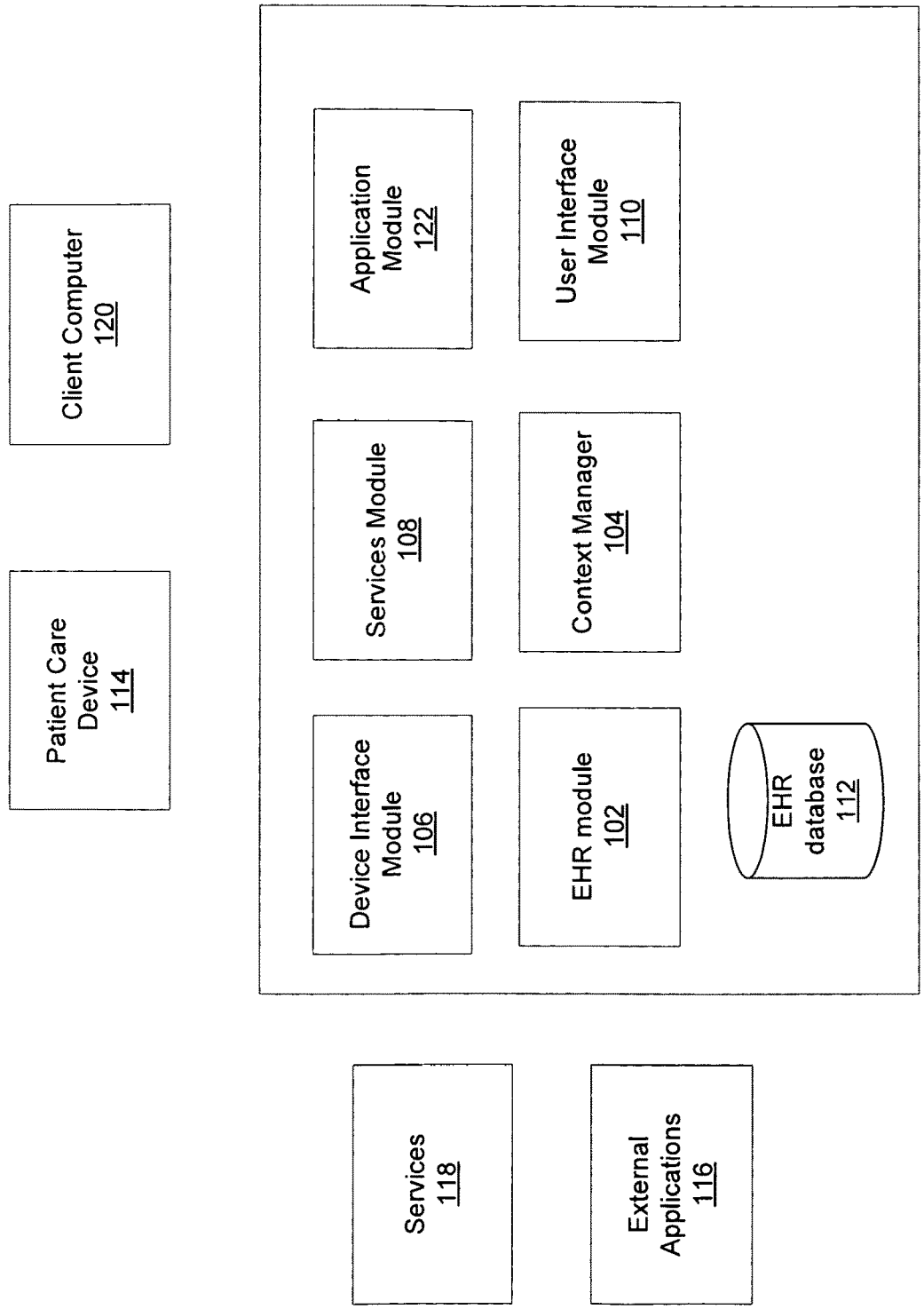
FIG. 1 illustrates a system for providing universal application integration in accordance with an embodiment of the present invention.

FIG. 1 illustrates a block diagram of a system 100 for providing universal application integration in accordance with an embodiment of the present invention. System 100 includes an EHR module 102, EHR database 112, context manager 104, device interface module 106, services module 108, user interface module 110, and application module 122. Also shown in FIG. 1 are patient care device 114, external applications 116, services 118, and client computer 120. For clarity of illustration, only one instance of each described element is included in FIG. 1. When implemented, however, multiple instances may be present—for example, as described below, there are a large number of different patient care devices in use. The depiction of these elements in the singular is therefore not intended to be limiting.

System 100 in one embodiment is a software application stored on computer readable medium such as a hard drive. In a first alternate embodiment, system 100 is embodied in hardware; in a second alternate embodiment, system 100 is embodied in a combination of hardware and software modules. In still other embodiments, the described modules are distributed over multiple networked systems.

Context manager 104 provides context information to and receives context information from external applications, services and patient care devices. Context information includes patient bibliographic data, procedure codes, billing information, and the like, and is supplied or obtained based on the current context. EHR database 112 stores the electronic health records of patients. Patient health records are read from and written to database 112 by EHR module 102. EHR module 102 also provides an interface to client computer 120, which is operated, for example, by a doctor or clinician in an exam or testing room. Device interface module 106 communicates with patient care device 114 to acquire data such as vital statistics and other measurements from the device. Services module 108 provides output to external services 118. System 100 includes a user interface (UI) module 110 that allows for configuration of the system depending on the environment in which it is implemented.

Figure 2:
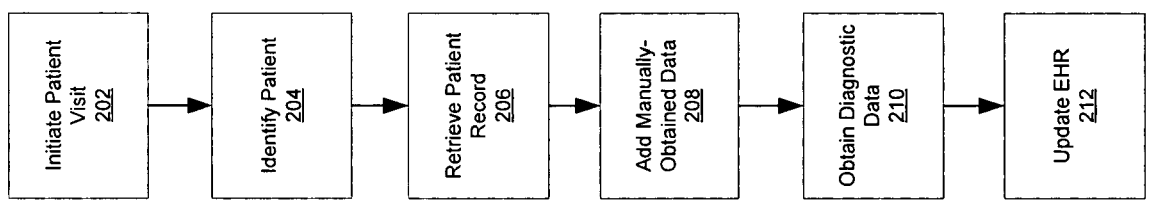
FIG. 2 is a flowchart illustrating a method for providing universal application integration in accordance with an embodiment of the present invention.

FIG. 2 provides a flowchart of a method for providing universal application integration in the context of a patient visit, and in accordance with an embodiment of the present invention.

A visit begins with the arrival of a patient. A health care worker, e.g., a doctor, nurse, clinician or technician, uses client computer 120 to initiate 202 the visit. In one embodiment, the health care worker identifies 204 the patient by selecting the patient's name from an electronic appointment list. Alternatively, the patient may have an RFID-enabled identification device, a barcode, card with a magnetic stripe, or may be identified by fingerprint or other means. Context manager 104 receives the patient identifier information and instructs EHR module 102 to retrieve 206 the patient's record from EHR database 112, or to create a patient record if one does not yet exist. In one embodiment, EHR module displays the patient's health record to the health care worker by supplying it to an application program 116 executing on client 120. In one embodiment, an application program for patient management is included in system 100 and is accessed by health care workers through UI module 110. In one embodiment, UI module 110 is accessed over a network using a web browser such as Microsoft Internet Explorer or Mozilla Firefox.

If the health care worker obtains information manually, for example by measuring the patient's height and weight, that data is provided to system 100 and used to update 208 the patient's EHR.

Next, patient diagnostic data is obtained 210 for the patient. FIG. 3 illustrates acquisition of patient diagnostic data by device interface module 106. A patient care device 114 is used to obtain measurements and/or observations from or about a patient 302. Many kinds of patient care devices are in use today, such as tools for obtaining vital statistics such as body temperature and blood pressure, monitoring heart and respiratory functions, testing vision, etc. As will be appreciated by those of skill in the art, any measurement data or observations that are capturable by a patient care device 114 are useable with system 100. For ease of description, patient diagnostic data is intended to refer to such measurement data or observations obtained by the patient care device.

Device interface 106 in one embodiment includes an application driver layer/framework that enables a standardized method for integrating data from a patient care device 114 into an EHR. This is done by standardizing the wrapper/driver layer as well as standardizing the vocabulary and terminology around the information captured. In one embodiment, SNOMED terminology is used; in an alternative embodiment, LOINC terminology is used. In additional embodiments, still other standardized terminologies are used.

In one embodiment, patient care device 114 is configured to accept data from system 100. In this embodiment, context manager 104 provides context information to the device such as patient bibliographic data and any additional data required to configure the patient care device 114. The device is then used to obtain the diagnostic data.

Once patient diagnostic data is acquired by device interface module 106, it is in one embodiment provided to EHR module 102, which in turn writes 212 (FIG. 2) the diagnostic data to EHR 112, as well as providing the data to a clinician via client computer 120. In addition, services module 108 can be configured to trigger a billing entry to be sent to an external service such as a billing service in response to the particular diagnostic function undertaken.

For example, a health care worker uses a patient care device 114 to obtain the patient's temperature and blood pressure. Device interface module 106 obtains the patient diagnostic module from patient care device 114 and displays the obtained data to the health care worker via client 120. In one embodiment, the data is automatically written to the patient's EHR by EHR module 102. Alternatively, a health care worker reviews the data before it is written to the record, either confirming it or instructing system 100 to discard the data. In this manner, the patient's EHR is populated automatically using the acquired data, obviating the need for a clinician to input the data manually, and avoiding a potential source of mix up or other error.

In some implementations, it is desirable to store some patient diagnostic data is in locations other than or in addition to the patient's EHR. For example, a patient may have been wearing a heart monitor for a 24-hour period, and the recorded data requires evaluation by a cardiologist. In one embodiment, after device interface module 106 acquires the diagnostic data—in this case, the heart monitor's output—services module 108 provides that data to a service 118 such as a cardiologist's electronic analysis queue. Additional application of services module 108 includes providing paper-based output or document capture for communicating with external applications that are not capable of interfacing with system 100.

In one embodiment, service 118 is a billing module, and services module 108 provides to the billing module an indication of the completed task—in this case, a 24-hour heart monitor.

System 100 additionally supports two-way communication with external applications 116. In one embodiment, communication is enabled through use by system 100 and external applications 116 of web-services based on the SOAP 1.1 or 1.2 specification. For example, in the context of the cardiovascular analysis described above, a specialized cardio application may exist for use by a reviewing cardiologist, and applications module 122 establishes a connection to the cardio application and provides the data acquired from the patient care device 114 directly to the application. Context manager 104 optionally also provides bibliographic and other information to the external application.

Similarly, system 100 acquires data provided by an external application 116. Continuing the above example, once a cardiologist has reviewed the patient's monitor data, the cardio application establishes a connection with application module 122 and provides the cardiologist's conclusions and any additional relevant data. System 100 then writes the received data to the patent's EHR, and in one embodiment sets a flag to alert a designated health care worker that the patient's record has been updated. Since system 100 automatically populates relevant fields of the patient's EHR, the clinician need only review the data and take any appropriate next steps, without having to first enter the data provided by the external application.

The automatic population of health record data and integration of multiple applications enables the availability of information in real-time. This allows health care providers to have the most up-to-date information possible when making diagnoses and treatment decisions for patients.

In some cases, data is not immediately available from a patient care device, such as where a patient wears a monitoring device for an extended period of time. In one embodiment, data from such a device is provided to device interface module 106 after the patient returns the device. In another alternative embodiment, data is uploaded from the device to system 100 while the device is still in use by the patient. For example, the device uploads to system 100 via a telephone/acoustic coupler connection, via a modem, via the Internet using a connection to the patient's own PC, or via RF to a device located in the patient's home.

In one embodiment, a document scanner, for example attached to client computer 120, captures documents and uploads them to system 100, where EHR module 102 automatically associates the captured documents with the patient's health record. This allows, for example, medical records from another facility to be immediately made available for review, and avoids the potential for lost or misidentified records.

In one embodiment, system 100 additionally includes a configurable rules processor that enables the automated generation of tasks. For example, a protocol might state that if a patient's blood pressure is above a certain level, the clinician is to alert the doctor. System 100 automatically alerts the doctor, e.g., via a pager, e-mail, broadcast announcement, etc., as soon as the vitals information is received from patient care device 114. This eliminates the need to have the clinician remember the protocol and avoids the risk of the protocol not being followed.

The present invention has been described in particular detail with respect to a limited number of embodiments. One skilled in the art will appreciate that the invention may additionally be practiced in other embodiments. First, the particular naming of the components, capitalization of terms, the attributes, data structures, or any other programming or structural aspect is not mandatory or significant, and the mechanisms that implement the invention or its features may have different names, formats, or protocols. Further, the system may be implemented via a combination of hardware and software, as described, or entirely in hardware elements. Also, the particular division of functionality between the various system components described herein is merely exemplary, and not mandatory; functions performed by a single system component may instead be performed by multiple components, and functions performed by multiple components may instead performed by a single component. For example, the particular functions of the map data provider, map image provider and so forth may be provided in many or one module.

Some portions of the above description present the feature of the present invention in terms of algorithms and symbolic representations of operations on information. These algorithmic descriptions and representations are the means used by those skilled in the art to most effectively convey the substance of their work to others skilled in the art. These operations, while described functionally or logically, are understood to be implemented by computer programs. Furthermore, it has also proven convenient at times, to refer to these arrangements of operations as modules or code devices, without loss of generality.

It should be borne in mind, however, that all of these and similar terms are to be associated with the appropriate physical quantities and are merely convenient labels applied to these quantities. Unless specifically stated otherwise as apparent from the present discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the present invention include process steps and instructions described herein in the form of an algorithm. It should be noted that the process steps and instructions of the present invention could be embodied in software, firmware or hardware, and when embodied in software, could be downloaded to reside on and be operated from different platforms used by real time network operating systems.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and displays presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will appear from the description above. In addition, the present invention is not described with reference to any particular programming language. It is appreciated that a variety of programming languages may be used to implement the teachings of the present invention as described herein, and any references to specific languages are provided for disclosure of enablement and best mode of the present invention.

The figures depict preferred embodiments of the present invention for purposes of illustration only. One skilled in the art will readily recognize from the following discussion that alternative embodiments of the structures and methods illustrated herein may be employed without departing from the principles of the invention described herein.

Finally, it should be noted that the language used in the specification has been principally selected for readability and instructional purposes, and may not have been selected to delineate or circumscribe the inventive subject matter.

Accordingly, the disclosure of the present invention is intended to be illustrative, but not limiting, of the scope of the invention.

We claim:

1. A networked electronic health record (ERR) computer system enabling electronic access to patient data of electronic health records (ERRs), comprising:
   an ERR database, which stores ERRs for a plurality of patients;
   an ERR module, which reads and writes patient data to ERRs in the ERR database;
   a device interface module comprising an application driver layer or framework configured to receive, from a plurality of patient care devices (PCDs), patient diagnostic data in different formats, and standardize the received patient diagnostic data to an integrated format of the ERRs stored in the ERR database;
   a context manager, which provides context information to and receives context information from each of the plurality of PCDs, applications, and services, wherein the context information for a particular communication is based at least in part on the respective PCD, respective application, or respective service of the communication;
   a service module, which provides information to each of a plurality of services for supporting performance of the respective service, the information provided to a particular service being in a format usable by the service; and
   an application module, which, electronically provides patient data from the ERRs to each of a plurality of applications, the patient data electronically provided to a particular application being in a format that usable by the application, and receives patient data from each of the plurality of applications for saving in the ERRs of the ERR computer system;
   wherein the context manager is configured to provide a first instance of context information to a first PCD, the first instance of context information comprising at least one of patient bibliographic data, procedure codes, and billing information for a particular patient,
   wherein the device interface module is configured to receive patient diagnostic data from the first PCD in response to the provided first instance of context information, and save the patient diagnostic data in a respective ERR for the particular patient that is stored in the ERR database, by writing of the patient diagnostic data by the ERR module to the respective ERR for the particular patient, and set a flag indicating that the ERR of the particular patient has been updated by patient data.

2. The ERR computer system of claim 1, wherein the patient bibliographic data comprises at least one of (i) a unique patient identifier that identifies the patient in the networked ERR computer system, (i) a patient's name, (i) a patient's address, and (ii) a patient's date of birth.

3. The ERR computer system of claim 1, wherein the application module communicates with an application over the Internet.

4. The ERR computer system of claim 1, wherein the context manager receives patient identifier information and causes the ERR module to retrieve the respective ERR of the patient from the ERR database based on the patient identifier information.

5. The ERR computer system of claim 1, wherein the service module automatically provides information to a billing service upon receipt of particular patient diagnostic data by the device interface module.

6. The ERR computer system of claim 1, wherein the service module provides information to a service by causing a paper-based output of the information at an applicable physical location associated with the service.

7. The ERR computer system of claim 1, wherein the service module provides information to a service by causing electronic document capture of the information by an application associated with the service.

8. The ERR computer system of claim 1, wherein the system further comprises a configurable rules processor that enables the automated generation of tasks based on patient diagnostic data that is received by the device interface module.

9. The ERR computer system of claim 1, wherein the system further comprises a configurable rules processor that automatically generates an alert based on patient diagnostic data that is received by the device interface module.

10. The ERR computer system of claim 1, wherein the plurality of PCDs comprise a PCD configured to measure a patient's heart rate.

11. The ERR computer system of claim 1, wherein the plurality of PCDs comprise a PCD configured to measure a patient's blood pressure.

12. The ERR computer system of claim 1, wherein the plurality of PCDs comprise a PCD configured to measure a patient's temperature.

13. A method of operating a networked electronic health record (ERR) computer system enabling electronic access to patient data of electronic health records (ERRs), comprising:
   storing ERRs for a plurality of patients in an ERR database;
   reading and writing patient data to ERRs in the ERR database via an ERR module;
   receiving, via a device interface module comprising an application driver layer or framework, patient diagnostic data in different formats from a plurality of patient care devices (PCDs);
   standardizing, via the device interface module, the received patient diagnostic data to an integrated format of the ERRs stored in the ERR database;
   electronically providing, via a context manager, context information to and receiving context information from each of the plurality of PCDs, applications, and services, wherein the context information for a particular communication is based at least in part on the respective PCD, respective application, or respective service of the communication;
   electronically providing, via a service module, information to each of a plurality of services for supporting performance of the respective service, the information provided to a particular service being in a format usable by the service;
   electronically providing, via an application module, patient data from the ERRs to each of a plurality of applications, the patient data electronically provided to a particular application being in a format that usable by the application, and receives patient data from each of the plurality of applications for saving in the ERRs of the ERR computer system; and
   electronically providing, via the context manager, a first instance of context information to a first PCD, the first instance of context information comprising at least one of patient bibliographic data, procedure codes, and billing information for a particular patient, receiving, via the device interface module, patient diagnostic data from the first PCD in response to the provided first instance of context information, and saving the patient diagnostic data in a respective ERR for the particular patient that is stored in the ERR database, by writing the patient diagnostic data by the ERR module to the respective ERR for the particular patient, and setting a flag indicating that the ERR of the particular patient has been updated by patient data.

14. The method of claim 13, wherein the patient bibliographic data comprises at least one of (i) a unique patient identifier that identifies the patient in the networked ERR computer system, (i) a patient's name, (i) a patient's address, and (ii) a patient's date of birth.

15. The method of claim 13, wherein electronically providing, via the application module, patient data comprises communicating with an application over the Internet.

16. The method of claim 13, further comprising receiving, via the context manager, patient identifier information and causing the ERR module to retrieve the respective ERR of the patient from the ERR database based on the patient identifier information.

17. The method of claim 13, further comprising automatically providing, via the service module, information to a billing service upon receipt of particular patient diagnostic data by the device interface module.

18. The method of claim 13, further comprising providing, via the service module, information to a service by causing a paper-based output of the information at an applicable physical location associated with the service.

19. The method of claim 13, further comprising providing, via the service module, information to a service by causing electronic document capture of the information by an application associated with the service.

20. The method of claim 13, further comprising enabling, via a configurable rules processor, an automated generation of tasks based on patient diagnostic data that is received by the device interface module.

21. The method of claim 13, further comprising automatically generating, via a configurable rules processor, an alert based on patient diagnostic data that is received by the device interface module.

\* \* \* \* \*